United States Patent [19]
Barnwell

[11] Patent Number: 5,874,527
[45] Date of Patent: Feb. 23, 1999

[54] PLASMODIUM VIVAX BLOOD STAGE ANTIGENS

[75] Inventor: John W. Barnwell, New York, N.Y.

[73] Assignee: New York University, New York, N.Y.

[21] Appl. No.: 719,822

[22] Filed: Sep. 30, 1996

Related U.S. Application Data

[63] Continuation of Ser. No. 478,417, Jun. 7, 1995, abandoned, which is a continuation of Ser. No. 72,610, Jun. 2, 1993, Pat. No. 5,532,133.

[51] Int. Cl.$^6$ .......................... A61K 38/00; A61K 39/015
[52] U.S. Cl. ........................ 530/300; 530/350; 530/388.6; 424/184.1; 424/185.1; 424/191.1; 424/268.1
[58] Field of Search ..................................... 530/300, 350, 530/403, 820, 822, 388.1, 388.6; 435/947; 424/184.1, 185.1, 190.1, 272.1

*Primary Examiner*—Patricia Duffy
*Attorney, Agent, or Firm*—Darby & Darby

[57] ABSTRACT

This invention is directed to novel species-specific *P. vivax* malarial peptide antigens which are proteins or fragments of proteins secreted into the plasma of a susceptible mammalian host after infection, and to monoclonal or polyclonal antibodies directed against those antigens. The peptide antigens, monoclonal antibodies, and/or polyclonal antibodies are utilized in assays used to diagnose malaria, as well as to determine whether *Plasmodium vivax* is the species responsible for the infection.

3 Claims, 9 Drawing Sheets

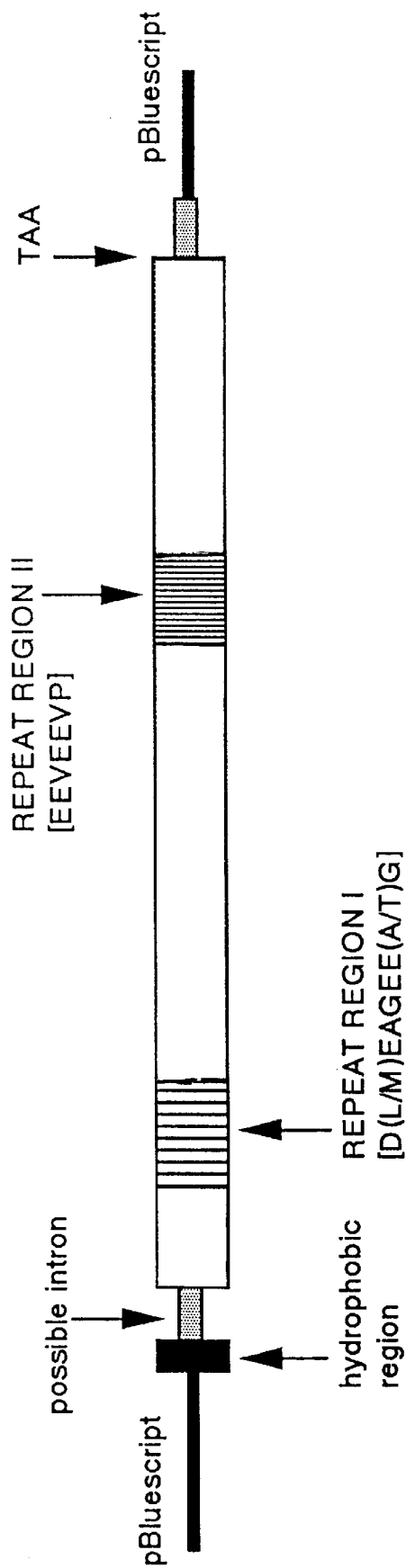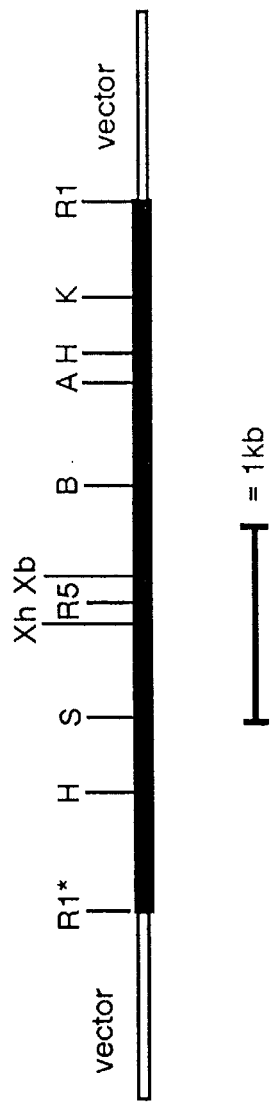
FIG. 3A
FIG. 3B

FIG. 4A
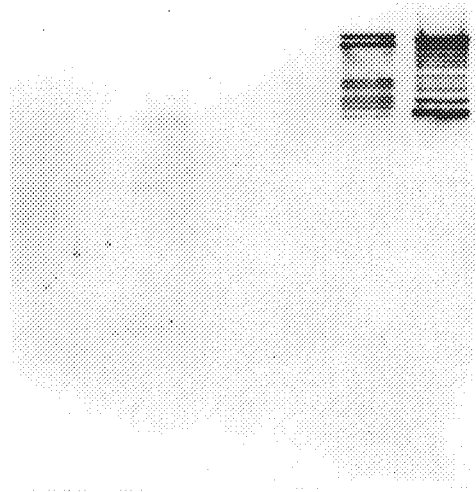
FIG. 4B
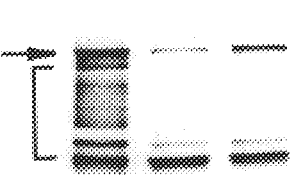
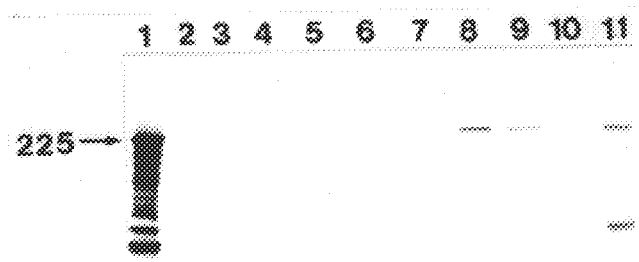
FIG. 4C
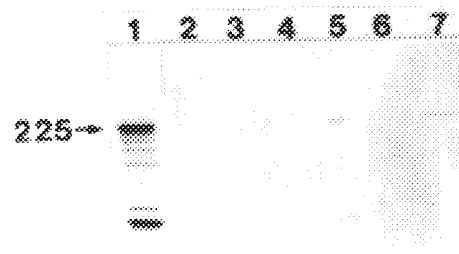
FIG. 4D

FIG. 5A

```
                                                                    G
AATTCCGGTAAAGTAACAACTATGGTTTCGTATCTATATATAACCTTACTAATTTTATCT  61
  N  S  G  K  V  T  T  M  V  S  Y  L  Y  I  T  L  L  I  L  S
TTTGCTTTTCTTTTAATTCATGCTTCAACAGTAAGATAAAAATAATCTATAAAAACTGC  120
  F  A  F  L  L  I  H  A  S  T
TATATATACATATATATTCATAAGTGGCATTTGTGAATTGCGATCATTTAAATTTACGTA  180

AAAACAATATTGAAAAAAATTTTTTTTTTTTTTTTTTTGTTCTACAGAACGATTTAG  240
                                                  N  D  L
AATTGGAAAATGCTTCTGATGATGTTGTAGAGGTGGAGGATCCTTCAAACGACGGTTTAG  300
  E  L  E  N  A  S  D  D  V  V  E  V  E  D  P  S  N  D  G  L
AATTAGAAGAGGAAAATTTTGATGAGAATTCAGGTGATGATGAAACTCTTTTAGATGCTA  360
  E  L  E  E  E  N  F  D  E  N  S  G  D  D  E  T  L  L  D  A
CCCCCGAAGATGACTTTGCCTTAACAGATTTGCCAATTGAAGACGATGAGGAAGTCAACG  420
  T  P  E  D  D  F  A  L  T  D  L  P  I  E  D  D  E  V  N
AAACGTTAGATGGAGGTGAATCATTAGGAGAGGTTTCCACTGAAGATATGGAAACAGAAG  480
  E  T  L  D  G  G  E  S  L  G  E  V  S  T  E  D  M  E  T  E
ATGGCTCAACAGATGATACGGAAACAGAAGAAGGACTACCTGGTGATATGGAAGGAGAAG  540
  D  G  S  T  D  D  T  E  T  E  E  G  L  P  G  D  M  E  G  E
AAGAAGCTGGCGATATGGAAGCAGGGGAAGAAGCTGGTGATTTGGAAGCAGGGGAAGAAA  600
  E  E  A  G  D  M  E  A  G  E  E  A  G  D  L  E  A  G  E  E
CTGGCGATTTGGAAGCAGGGGAAGAAACTGGCGATTTGGAAGCAGGGGAAGAAGCTGGTG  660
  T  G  D  L  E  A  G  E  E  T  G  D  L  E  A  G  E  E  A  G
ATTTGGAAGCAGGGGAAGAAACTGGCGATTTGGAAGCAGGGGAAGAAACTGGAGATGCGG  720
  D  L  E  A  G  E  E  T  G  D  L  E  A  G  E  E  T  G  D  A
AAACTGAAGAAGGAGCAACTGGAGATGCGGAAACTGAAAATGGAGCAACTGTGTATGTAG  780
  E  T  E  E  G  A  T  G  D  A  E  T  E  N  G  A  T  V  Y  V
ACACAGAAGATAGTTCAGCTGATGGAGCAGAAAAAGTACATGTTCCTGCTCAAGAAAATG  840
  D  T  E  D  S  S  A  D  G  A  E  K  V  H  V  P  A  Q  E  N
TACAACCTGCCGATAGTAATGATGCCCTCTTTGGAAGTATTTTGGATAAAGATATAATTT  900
  V  Q  P  A  D  S  N  D  A  L  F  G  S  I  L  D  K  D  I  I
TTGATCATATTAAAGATTTCGAGCCACTATTCGAACAAATTGTGGCGGGTACTGCTAAAC  960
  F  D  H  I  K  D  F  E  P  L  F  E  Q  I  V  A  G  T  A  K
ATGTTACGGGACAAGAATTGCCAATGAAACCTGTACCATTACCAGTGGCAGAAGAGCCCG  1020
  H  V  T  G  Q  E  L  P  M  K  P  V  P  L  P  V  A  E  E  P
CGCAAGTACCAGCGGAAGAATTAGATGCCACTCCAGAGGATGACTTCGCATTAGATGTTA  1080
  A  Q  V  P  A  E  E  L  D  A  T  P  E  D  D  F  A  L  D  V
CAGAATCTCCCGAGGAAGTAGAATTAGTATTAGATGAAGAGGCAACTGAAGAAGAATCAA  1140
  T  E  S  P  E  E  V  E  L  V  L  D  E  E  A  T  E  E  S
CGGAAGTGGGACCAACGGAAGAAGGACCAACCGAAGAATTAGATGCCACTCCAGAGGATG  1200
  T  E  V  G  P  T  E  E  G  P  T  E  E  L  D  A  T  P  E  D
GATTTCGCATTAGACGAAACTGCAGAAGGAGAAACAGAAGAAACGTAGAGGGAGAAGAAA  1260
  G  F  R  I  R  R  N  C  R  R  R  N  R  R  N  V  E  G  E  E
CAGAAGAAGCTGCAGAAGGAGAAGTATCAGAAGAAACTCCAGAAGGAGAAGAAGAGTTAG  1320
  T  E  E  A  A  E  G  E  V  S  E  E  T  P  E  G  E  E  E  L
AGGCAACTCCAGAGGATGATTTCGCATTAGATGGAACTACATTAGAAGAAACCGAAGAAA  1380
  E  A  T  P  E  D  D  F  A  L  D  G  T  T  L  E  E  T  E  E
CTGCAGAAGGAGAAGAAACCGTAGAGGGAGAAGAAACCGTAGAGGGAGAAGAAACCGTAG  1440
  T  A  E  G  E  E  T  V  E  G  E  E  T  V  E  G  E  E  T  V
AGGGAGAAGAAGCTGCAGAAGGAGAAGAAGAGTTAGAGGCAACTCCAGAGGATGACTTCC  1500
  E  G  E  E  A  A  E  G  E  E  E  L  E  A  T  P  E  D  D  F
AATTAGAAGAACCATCAGGAGAAGGAGAAGGGGAAGGAGAAGGAGAAGGGGAAGGAGAAG  1560
  Q  L  E  E  P  S  G  E  G  E  G  E  G  E  G  E  G  E  G  E
```

```
A─────────────────────────────────────────────────────────────────A
GAGAAGCGTTAGTAGCAGTGCCAGTAGTGGCCGAACCGGTAGAAGTAGTGACTCCTGCTC 1620
 G  E  A  L  V  A  V  P  V  V  A  E  P  V  E  V  V  T  P  A
AGCCTGTCAAACCAATGGTCGCTCCAACGGCAGATGAAACTTTATTCGTTGATATCTTAG 1680
 Q  P  V  K  P  M  V  A  P  T  A  D  E  T  L  F  V  D  I ·L
ATAACGATTTAACGTATGCAGACATTACATCCTTTGAGCCATTATTTAAACAAATCCTCA 1740
 D  N  D  L  T  Y  A  D  I  T  S  F  E  P  L  F  K  Q  I  L
AGGATCCTGATGCAGGAGAGGCTGTAACAGTACCATCAAAGGAAGCACCTGTACAAGTAC 1800
 D  D  P  D  A  G  E  A  V  T  V  P  S  K  E  A  P  V  Q  V
CAGTGGCAGTAGGGCCCGCGCAAGAAGTGCCAACGGAAGAATTGATGCAACTCCAAGAGG 1860
 P  V  A  V  G  P  A  Q  E  V  P  T  E  E  L  M  Q  L  Q  E
ACGATTTCGAATTAGAAGGAACTGCAGAAGCTCCAGAGGAAGGAGAATTAGTATTAGAAG 1920
 D  D  F  E  L  E  G  T  A  E  A  P  E  E  G  E  L  V  L  E
GAGAAGGAGAACCAACGGAAGAAGAGCCAAGAGAAGGAGAGCCAACAGAAGGAGAAGTGC 1980
 G  E  G  E  P  T  E  E  E  P  R  E  G  E  P  T  E  G  E  V
CAGAAGAAGAATTAGAGGCAACTCCAGAGGACGATTTCGAATTAGAAGAACCAACAGGAG 2040
 P  E  E  E  L  E  A  T  P  E  D  D  F  E  L  E  E  P  T  G
AAGAAGTAGAAGAAACCGTAGAGGGCGAAGAAACTGCAGAAGGAGAAGAAGTGGAAGAGG 2100
 E  E  V  E  E  T  V  E  G  E  E  T  A  E  G  E̲  E̲  V̲  E̲  E̲
TACCTGCAGAAGTAGAAGAAGTGGAAGAGGTACCTGCAGAAGTAGAAGAAGTGGAAGAGG 2160
 V̲  P̲  A  E  V̲  E̲  E̲  V̲  E̲  E̲  V̲  P̲  A  E  V̲  E̲  E̲  V̲  E̲  E̲
TACCAGAAGAAGTAGAAGAGGTACCCGCAGAAGTAGAAGAAGTGGAAGAGGTACCAGAAG 2220
 V̲  P̲  E̲  E̲  V̲  E̲  E̲  V̲  P̲  A  E  V̲  E̲  E̲  V̲  E̲  E̲  V̲  P̲  E̲
AAGTGGAAGAGGTACCAGAAGAAGTGGAAGAGGTACCAGAAGAAGTGGAAGAGGTACCAG 2280
 E̲  V̲  E̲  E̲  V̲  P̲  E̲  E̲  V̲  E̲  E̲  V̲  P̲  E̲  E̲  V̲  E̲  E̲  V̲  P̲
AAGAAGTGGAAGAAGTGGAAGAAGTAGAAGAAGTAGAGGTACCAGCGGTAGTAGAAGTAG 2340
 E̲  E̲  V̲  E̲  E̲  V̲  E̲  E̲  V̲  E̲  V̲  P̲  A  V  V  E  V
AAGTACCAGCGGTAGTAGAAGAAGAGGTGCCAGAAGAAGTAGAAGAAGAAGAAGAAGAGG 2400
 E  V  P  A  V  V  E  E  V  P  E  E  V  E  E  E  E
AAGAACCAGTAGAGGAAGAAGATGTATTACAATTAGTAATACCATCGGAAGAAGATATAC 2460
 E  E  P  V  E  E  E  D  V  L  Q  L  V  I  P  S  E  E  D  I
AATTAGACAAACCAAAGAAAGACGAATTAGGCTCTGGAATTTTATCTATCATCGACATGC 2520
 Q  L  D  K  P  K  K  D  E  L  G  S  G  I  L  S  I  I  D  M
ACTACCAAGACGTTCCAAAGGAATTTATGGAAGAAGAAGAAGAAACTGCAGTGTATCCAT 2580
 H  Y  Q  D  V  P  K  E  F  M  E  E  E  E  E  T  A  V  Y  P
TGAAACCAGAAGATTTTGCAAAGGAAGATTCACAATCTACAGAATGGCTCACATTCATTC 2640
 L  K  P  E  D  F  A  K  E  D  S  Q  S  T  E  W  L  T  F  I
AAGGCCTAGAAGGCGACTGGGAACGATTAGAAGTGAGCTTAAATAAGGCTAGAGAAAGAT 2700
 Q  G  L  E  G  D  W  E  R  L  E  V  S  L  N  K  A  R  E  R
GGATGGAACAAAGAAATAAAGAATGGGCTGGCTGGCTTCGCTTAATTGAAAATAAATGGT 2760
 W  M  E  Q  R  N  K  E  W  A  G  W  L  R  L  I  E  N  K  W
CAGAATATAGTCAAATTTCAACAAAAGGAAAGGACCCAGCTGGTTTGAGAAAACGAGAGT 2820
 S  E  Y  S  Q  I  S  T  K  G  K  D  P  A  G  L  R  K  R  E
GGAGCGACGAGAAATGGAAAAAATGGTTTAAAGCAGAAGTCAAATCCCAAATTGATTCAC 2880
 W  S  D  E  K  W  K  K  W  F  K  A  E  V  K  S  Q  I  D  S
ACTTGAAAAAATGGATGAACGACACTCATTCCAATTTATTTAAAATTCTTGTGAAAGATA 2940
 H  L  K  K  W  M  N  D  T  H  S  N  L  F  K  I  L  V  K  D
B─────────────────────────────────────────────────────────────────B
```

TGTCACAATTTGAAAACAAGAAAACCAAAGAATGGTTAATGAATCACTGGAAAAAGAACG 3000
 M  S  Q  F  E  N  K  K  T  K  E  W  L  M  N  H  W  K  K  N
AACGGGGTTATGGTTCTGAATCATTTGAAGTTATGACCACATCAAAATTATTAAATGTGG 3060
 E  R  G  Y  G  S  E  S  F  E  V  M  T  T  S  K  L  L  N  V
CTAAGAGTCGAGAATGGTACCGTGCCAATCCTAATATAAATAGAGAAAGAAGAGAACTCA 3120
 A  K  S  R  E  W  Y  R  A  N  P  N  I  N  R  E  R  R  E  L
TGAAATGGTTTCTCCTAAAAGAAAACGAATATTTAGGACAAAGAATGGAAAAAATGGACT 3180
 M  K  W  F  L  L  K  E  N  E  Y  L  G  Q  R  M  E  K  M  D
CATTGGAAAAAAGTTAAATTTTTTGTGTTCAATTCAATGTGTACAACATTTTCTGGAAAA 3240
 S  L  E  K  S
CGCCTAACCAAGGAAGAATGGAATCAATTTGTTAATGAAATAAAAGTTTGAATTATAGAA 3300

AAAAGAACAGATTATTCTCTTATAAAATAAATAATTC                        3337
```

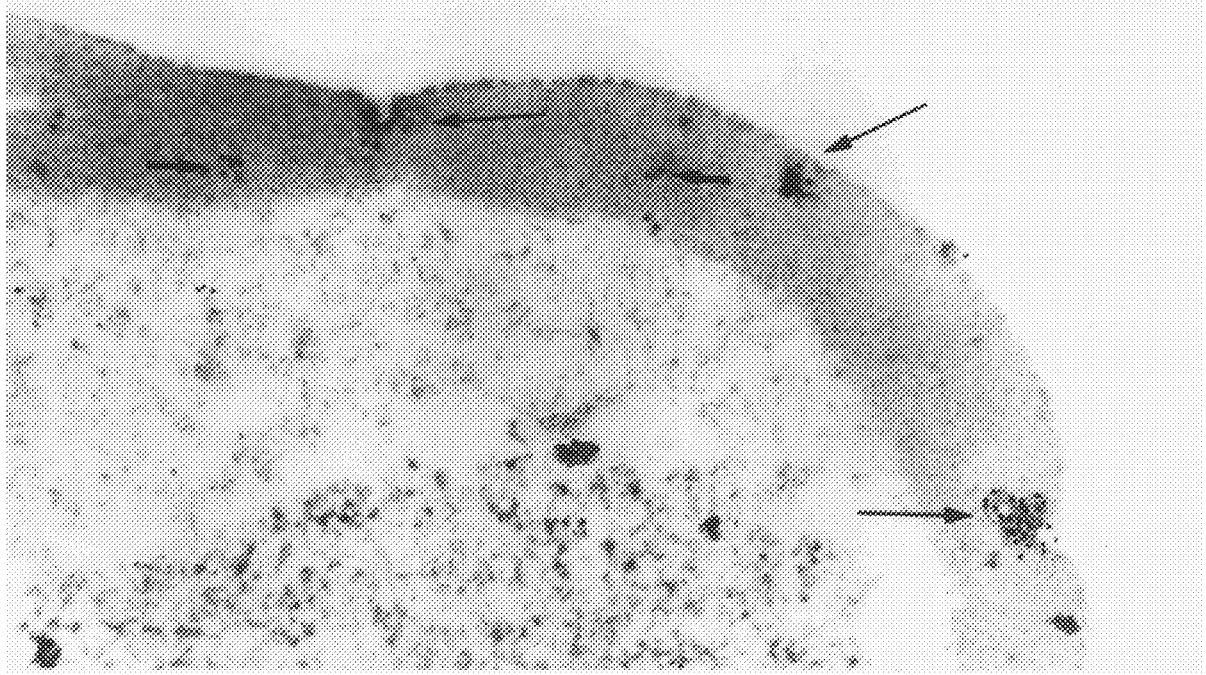

PLASMODIUM VIVAX BLOOD STAGE ANTIGENS

This is a continuation of application Ser. No. 08/478,417, filed Jun. 7, 1995 now abandoned, which is a continuation of application Ser. No. 08/072,610, filed Jun. 2, 1993 and issued on Jul. 2, 1996 as U.S. Pat. No. 5,532,133.

The U.S. Government has rights in this invention by virtue of Grant Nos. RO1 AI 24710 from The National Institutes of Health and DPE-5979-A-00-0006 from the Agency for International Development.

SUBJECT AREA OF THE INVENTION

This invention is directed to novel species-specific malarial polypeptides which are secreted into the plasma of a susceptible mammalian host after infection, and to antibodies directed against those proteins. The polypeptides and/or antibodies are utilized in assays used to diagnose malaria, as well as to determine whether *Plasmodium vivax* is the species responsible for the infection.

BACKGROUND OF THE INVENTION

Malaria is transmitted by the bite of the Anopheles mosquito. Minutes after infection, sporozoites (the mosquito-hosted stage of the malarial parasite) enter hepatocytes of the susceptible mammal where they multiply by schizogony and develop into merozoites. Rupture of the infected cells releases the merozoites into the blood, where they enter erythrocytes to begin a phase of asexual reproduction. During acute infections, malarial parasite protein antigens are known to be released, accumulate, and circulate in the plasma of infected individuals (Wilson et al., *The Lancet*, Jul. 26, 1969; Wilson et al., *International Journal for Parasitology* 3:511–520, 1973; Wilson et al., *Parasitology*, 71:183–192; Wilson, *Nature*, 284:451–452, 1980). The release of these antigens of parasitic origin can occur at the time that infected erythrocytes rupture to allow invasive merozoites to invade new red blood cells. The antigens that spill into the host plasma are those that have accumulated in the host cell cytoplasm and internal membranous structures.

Additionally, release of antigen can occur during the intraerythrocytic growth of the parasite as it matures from the ring stage, the stage which invades the erythrocyte, through the trophozoite stage, and into schizogony when the parasite differentiates into merozoites. Release of antigens at this time involves transport of the protein from the parasite across the parasitophorous vacuole and its membrane, across the host cell cytoplasm to the infected erythrocyte membrane, and then secretion as an intact soluble protein into the plasma of the host. One *P. falciparum* protein, PfHRP-2 (Histidine Rich Protein-2) has been described that follows this route of transport and is secreted into the culture supernatant or found in plasma (Wellems et al., *Proc. Natl. Acad. Sci. USA*, 83:6065–6069, 1986; Howard et al., *J. of Cell. Biol.*, 103:1269–1277, 1986; Rock et al., *Parasitology*, 95:209–227, 1987; Panton et al., *Mol. and Biochem. Parasitology*, 35:149–160, 1989). A search for HRP analogues in *P. vivax* using PfHRP gene probes and HRP-antisera gave only negative results (Rock et al., *Parasitology*, 95:209–227, 1987; J. Barnwell, unpublished results).

There is a need in the field for antibodies specific for a *P. vivax* blood stage protein in a diagnostic assay. The prior art assays based on antibodies specific for blood stage proteins have been specific only for *P. falciparum* (Khusmith, *Southeast Asian J Trop Med Public Health (THAILAND)*, 19:21-6, 1988) or have involved the use of panspecies-specific antibodies, so no existing assays are specific for *P. vivax* (Gao et al., *Southeast Asian J Trop Med Public Health (THAILAND)*, 22:393-6, 1991 and James, MA et al., American Society of Tropical Medicine and Hygiene, Seattle, Wash., Nov. 16–19, 1992, Abs. #135, pp. 145–146) *P. vivax* has latent liver stages, termed hypnozoites, which are reactivated and reinitiate blood stage parasitemias. Hypnozoites are eliminated by treatment with primaquine, but are not affected by chloroquine, which acts only on blood stage parasites. As *P. falciparum* does not produce hypnozoites, it is important to identify correctly the Plasmodium species responsible for infection in order to provide the appropriate course of chemotherapy for complete cure. The increased prevalence of drug resistant strains in certain species also makes it important to identify the species involved so correct chemotherapy can be given. Thus, there is a need for a method and reagents adapted for differential diagnosis of *P. vivax* malaria.

However, a number of criteria should be met by a particular protein antigen considered as a potential diagnostic target. First, it should be soluble and relatively stable and not rapidly degraded and/or rapidly removed from circulation. Second, the antigen should contain epitopes unique to a species to allow specific diagnosis and preferably be well-conserved within all or most isolates of a species. Additionally, it should be relatively abundant to allow detection at low parasitemia. As discussed below, the proteins of this invention fulfill most or all of these requirements.

SUMMARY OF THE INVENTION

Secreted species-specific blood stage antigens have now been identified from a major human malaria parasite species, *P. vivax*. Two particular such proteins are designated *P. vivax* Erythrocyte Secreted Protein-1 (PvESP-1) and *P. vivax* Erythrocyte Secreted Protein-2 (PvESP-2). These antigens and fragments thereof have unique *P. vivax*-specific epitopes which permits their use in differential determination of *P. vivax* merozoites. Antibodies can be and have been elicited against unique epitopes of such *P. vivax* proteins and used in assays which not only diagnose malaria, but also selectively identify *P. vivax* as the species having caused the infection.

DESCRIPTION OF THE DRAWINGS

FIG. 3A is a schematic representation of the *P. vivax* ESP-1 gene and structural features of the deduced protein. FIG. 3B is a partial restriction map of the *P. vivax* ESP-2 gene.

FIG. 4A is an immunoblot of *P. vivax* culture supernatants and plasma from *P. vivax* infected squirrel (Saimiri) monkeys. 4B is an immunoblot of multiple species of Plasmodium in multiple stages probed with PvESP-1 specific antibodies. FIGS. 4C and 4D are immunoblots of plasma from individuals infected with *P. falciparum*, *P. vivax* or both, and also probed with PvESP-1 specific antibodies. This group of figures shows the selective reaction of these antibodies with *P. vivax* and with proteins in the plasma of those infected with *P. vivax*. Similar results can be obtained with PvESP-2 antibodies using immunoblot procedures. (Example 5) Similar results for malaria specificity are also obtained for PvESP-1 or PvESP-2 antibodies on smears of different species of malaria parasites by indirect immunofluorescence assay.

FIG. 5 is the DNA sequence (SEQ ID NO:1) and deduced amino acid sequence (SEQ ID NO:2) of *P. vivax* ESP-1 (a sequence listing is provided separately).

DETAILED DESCRIPTION OF THE INVENTION

Figure 1A:
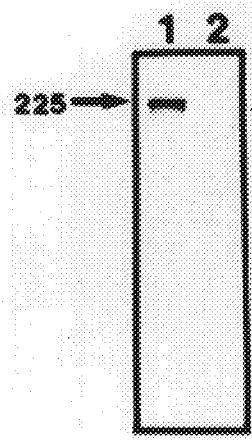
FIGS. 1A and 1B are Western immunoblots of *P. vivax* trophozoite infected erythrocytes probed with antibodies specific for PvESP-1 and PvESP-2. They show that mAb 1D11.G10 reacts with a 225 KD protein, while mAb 3D4.E2 and 1A3.B4 react with a 70 KD protein.

All U.S. patents and references referred to herein are hereby incorporated by reference in their entirety. In case of conflict, the present disclosure controls.

The following definitions apply to the terms as used in this application only and should not be construed to necessarily apply to uses of the terms in other art.

"Stringent conditions" are as defined by Southern et al. in *J. of Mol. Bio.*, 98:503 and as detailed in Maniatis, *Molecular Cloning: A Laboratory Manual*, 2nd ed., Chapter 9, 1989.

"Immunoreactive fragment" means a fragment of an antigen that is recognized by an antibody raised against the entire antigen.

"Immunoreactive analog" means a polypeptide which differs from a naturally occurring or recombinant protein by the substitution, deletion and/or addition of one or more amino acids but which retains the ability to be recognized by an antibody raised against the entire protein. A nonlimiting example is a carrier/antigen fusion polypeptide of the whole antigen or an immunoreactive fragment thereof, where the antigen or fragment can be embedded within the carrier polypeptide or linked to the carrier polypeptide at either end.

"Detecting" means determining the presence (or absence) or quantity of a substance (e.g. an antigen-antibody complex).

"Antibody" includes intact antibody molecule or fragments thereof that recognize antigen (e.g. Fab or F(ab')2 fragments) and can be of polyclonal or monoclonal type.

"Epitope" means any antigenic determinant responsible for immunochemical binding with an antibody molecule. Epitopes usually reside within chemically active surface groupings of protein molecules (including amino acids and often also sugar side-chains) and have specific three-dimensional structural characteristics and specific charge characteristics.

"Peptide Antigen" means a peptide, dipeptide, or polypeptide that can elicit (or react with) antibodies recognizing a particular protein.

The search for secreted blood stage antigens for *P. vivax* began by making monoclonal antibodies specific for blood stage parasites. As described in detail in Example 1, the mAbs were made by conventional techniques through the fusion of spleen cells isolated from a mouse immunized with *P. vivax* infected red blood cells with mouse myeloma cells to produce mAb secreting hybridomas. Three of these mAbs were found to react with the *P. vivax* proteins described herein. These proteins have been shown to be synthesized by the parasite by several criteria. First, mAbs do not react with uninfected erythrocytes as shown by control experiments and the specificity of the mAb for *P. vivax*, described in Example 6. A reaction to all species would be seen if the proteins were erythrocytic. Second, as seen by IFA and IEM, the mAbs do not react with uninfected erythrocytes which are present in the preparations. (See FIGS. 6 and 7) Third, the mAbs have been used to immunoprecipitate radiolabelled proteins from extracts of parasites that have been biosynthetically labelled with $^{35}$S-methionine. These results indicate that the mAbs recognize *P. vivax* proteins.

Figure 1B:
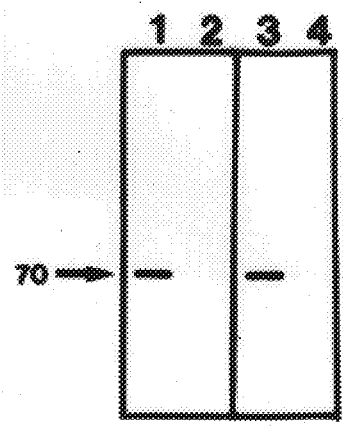
Figure 2A:
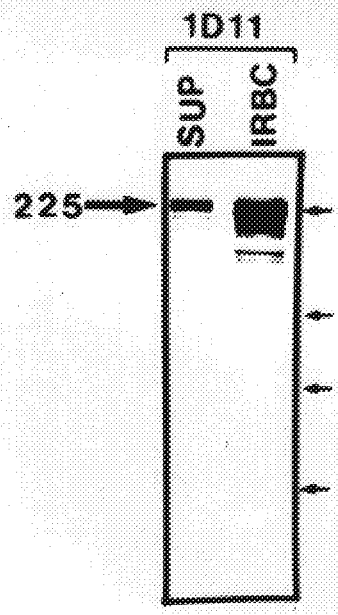
FIGS. 2A and 2B are Western immunoblots of *P. vivax* infected erythrocytes and supernatant from cultures which were matured from ring stage to late-staged trophozoites in vitro. The blots are probed with mAbs specific for PvESP-1 (2A) and PvESP-2 (2B). They show that both PvESP-1 and PvESP-2 are present in isolated infected erythrocytes and in the culture medium.
Figure 2B:
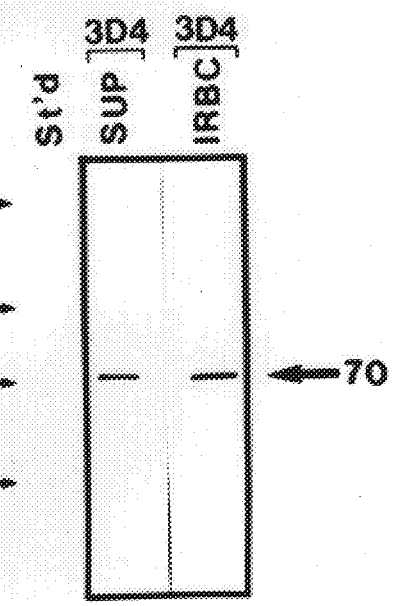
Figure 6A:
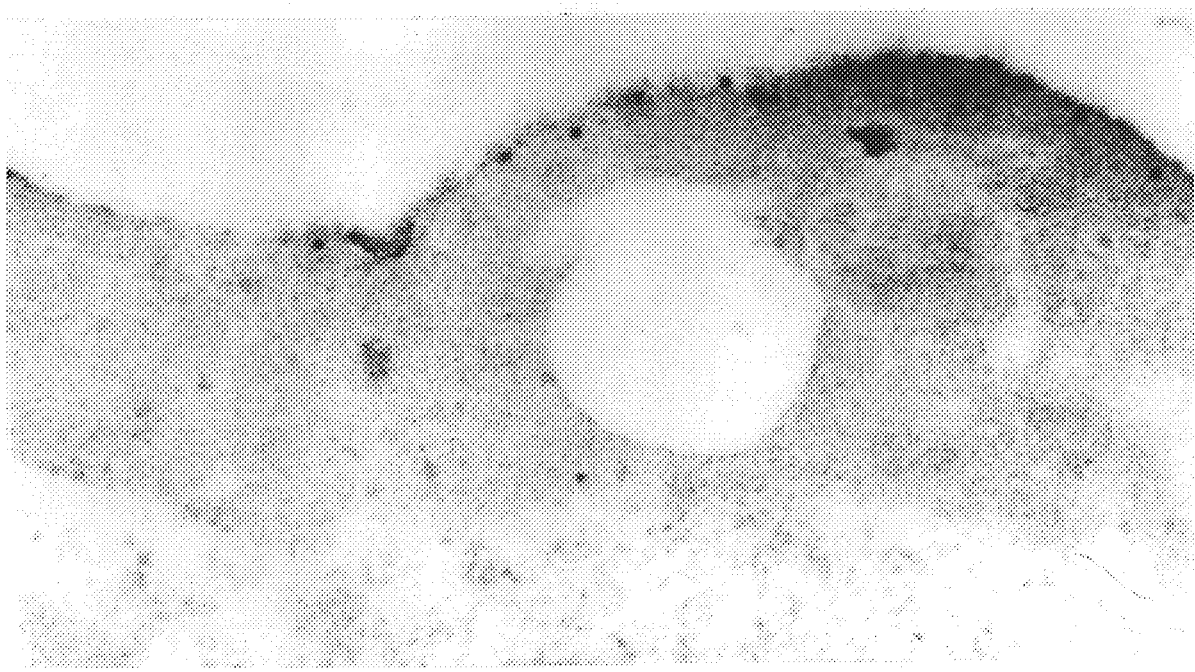
FIGS. 6A and B are the immunoelectron micrographs of *P. vivax* infected erythrocytes probed with mAb 1D11.G10 and mAb 3D4.A2, respectively.
Figure 7A:
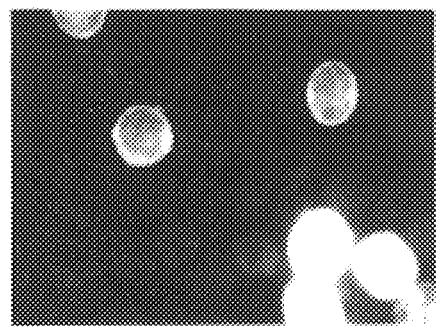
FIGS. 7A and B are immunofluorescent assays of *P. vivax* infected erythrocytes reacted with fluorescence-conjugated mAb 1D11.G10 and mAb 3D4.A2, respectively.
Figure 7B:
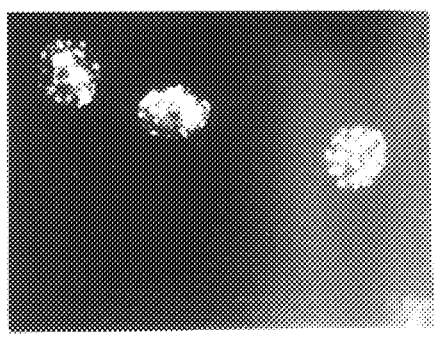

Specifically, mAb 1D11.G10 recognizes a *P. vivax* protein of approximately 225,000 daltons in size as judged by SDS-PAGE (FIG. 1A, lane 1). The hybridoma which produces mAb 1D11.G10 has been deposited with the American Type Culture Collection, 10801 University Boulevard, Manassas, Va. 20110 on May 26, 1993 and is Accession No. HB 11365. The protein recognized by this mAb has been designated *P. vivax*. ESP-1 or PvESP-1. It is found in the culture supernatant when intact infected erythrocytes are incubated in vitro for 10–24 hours (FIG. 2A, lane labelled SUP) as well as supernatant collected from in vitro cultures of rupturing mature schizont infected red cells (lane labelled IRBC). These data indicate that this protein is secreted. It is localized by inmunofluorescent assay (IFA) and immunoelectron microscopy (IEM) to the erythrocyte membrane of infected erythrocytes. (FIGS. 6A and 7A)

mAbs 3D4.A2 and 1A3.B4 recognize a *P. vivax* protein of approximately 70,000 daltons in size as judged by SDS-PAGE (FIG. 1B, lane 1). The hybridomas which produces mAbs 3D4.A2 and 1A3.B4 have been deposited with the American Type Culture Collection, 10801 University Boulevard, Manassas, Va. 20110 on May 26, 1993 and are Accession Nos. HB 11367 and HB 11366, respectively. The protein recognized by these mAb has been designated *P. vivax* ESP-2 or PvESP-2. Like PvESP-1, PvESP-2 is found in the supernatants of in vitro cultured intact trophozoite-infected erythrocytes (FIG. 2B, lane labelled SUP), and thus is a secreted protein. The PvESP-2 protein is also found in culture supernatants collected after schizont-infected erythrocytes have ruptured and released merozoites (lane labelled IRBC). The protein is localized by IFA and IEM to the caveola-vesicle complexes (CVC) of *P. vivax* infected erythrocytes. (FIGS. 6B and 7B.) The CVC are membranous sac-like vesicles attached to and contiguous with areas of flask-shaped indentations called caveolae in the erythrocyte plasma membrane.

Polyclonal antibodies can also be produced, for example, using isolated PvESP-1 and/or PvESP-2 or fragments thereof. General methodology for making such polyclonal antibodies is well-known in the art, and can be made using protocols similar to that described in Pink et al. (*Eur. J. Immunol.* 4:426–429, 1974).

The mAbs described above were used to screen a λZAP recombinant phage library of the *P. vivax* genome, although other equivalent *P. vivax* libraries could have been used. The preparation of this library is described in Example 2. After induction, mAb 1D11.G10 specifically recognized one plaque, designated PvMB3.3.1. The 3.34 kB plasmid insert was isolated and sequenced. The resulting sequence is SEQ ID No: 1. The nucleic acid sequence was analyzed for open reading frames (ORF) and the deduced amino acid sequence of the encoded protein was determined. The amino acid sequence is SEQ ID No: 2. A schematic structure of the gene and features of the encoded protein is presented in FIG. 3A. The gene appears to be missing a small portion of its 5' end.

As shown in FIGS. 3A and 5, the deduced amino acid sequence has an initial (N-terminal) sequence of hydrophobic amino acids. This is followed by a short 139 base pair (bp) intron with typical malaria intervening sequence splice sites. There follows a 2964 bp ORF, ending in the TAA stop codon which is 53 bp before the end of the cloned 3.34 kB insert DNA. A protein having this deduced peptide sequence is hydrophilic with a low pI (3), consistent with a large proportion of glutamate (Glu or E) residues in the deduced amino acid sequence.

As indicated in the Figures, there are two sets of repeated amino acid units in the sequence. One repeat unit is characterized by the sequence D(L/M)EAGEE(A/T)G residues 129 to 137, 138 to 146, 147 to 155, 156 to 164, 165 to 173, 174 to 182 and 183 to 191 of SEQ. ID NO:2. This sequence (SEQ ID NO:3) is repeated 7 times at the N-terminal end of the protein. The second repeat is located in the C-terminal portion of the protein, has the sequence EEVEEVP (SEQ ID NO:4) residues 649 to 655, 659 to 665, 669 to 675, 676 to 682, 686 to 692, 693 to 699, 700 to 706, 707 to 713, 714 to 722, and 723 to 728 of SEQ ID NO:2, and is repeated 10 times. The hydrophobic amino acid sequence could potentially be, as judged by its computer analyzed hydrophobicity profile, a transmembrane domain, or a leader or signal peptide sequence, or act as both. Completion of the 5' gene sequence will shed more light on these possibilities, and is well within the skill of the art in light of the present disclosure.

To determine the remainder of the gene sequence, the complete intact gene can be isolated and sequenced using a large DNA fragment, for example, in a Lambda replacement vector such as Lambda DASH (Stratagene, Lajolla, Calif.) or equivalent library using the insert as a probe. Methodology for this is provided by Galinski et al. (*Cell,* 69:1213–1226, 1992) or other similar methods. Alternatively, the 5' end could be isolated by the PCR amplification or other method of amplification of the cDNA using appropriate primers, for example, as described by Frohman et al. (*Proc. Natl. Acad. Sci. USA,* 85:8998–9002, 1988).

The MB3.3.1 plasmid expresses in *E. coli* a large recombinant protein recognized by the mAb 11D.G10 in Western immunoblots. The topmost band recognized is approximately 205–210 Kd in size, confirming that a small portion of the complete PvESP-1 gene remains unsequenced since the native protein migrates in SDS-PAGE at 225 Kd under identical conditions. This protein is easily isolated from the culture, using well-known techniques (Maniatis, *Molecular Cloning: A Laboratory Manual,* 2nd ed., Chapter 18, 1989). Mouse and rabbit antisera generated by immunization with the 1D11.G10 affinity purified recombinant protein recognizes both the recombinant and native PvESP-1 indicating that the recombinant phagmid MB3.3.1 authentically encodes PvESP-1.

Screening of the λZAPII expression libraries with the mAB 3D4.E2 revealed one phage plaque recognized by antibody. This clone, PvMB2.5.1, was found to contain a plasmid having a 3.7 kB insert. This plasmid has been deposited with the ATCC, Bethesda, Md. on May 26, 1993 having Accession No. 69318. A partial restriction map of the plasmid insert is depicted in FIG. 3B. The sequence of this DNA is easily obtainable using, e.g., traditional nested deletion and subcloning techniques or using nucleic acid primers obtained by dideoxy sequencing of the insert (Maniatis, *Molecular Cloning: A Laboratory Manual,* 2nd ed., Chapter 13, 1989).

The MB2.5.1 plasmid expresses a recombinant polypeptide of approximately 60 KD, which is easily isolated from the culture medium using standing protein isolation techniques (Maniatis, *Molecular Cloning: A Laboratory Manual,* 2nd ed., Chapter 18, 1989). The size of this protein suggests that a portion of the coding region of this protein is not present in the insert, as the native protein migrates under identical conditions in SDS-PAGE at approximately 70 KD. The 60 KD polypeptide is recognized by mAb 3D4.E2 in Western blots, indicating the recognized epitope is encoded by the insert. Additionally confirmation that plasmid MB 2.5.1 authentically encodes PvESP-2 can be done as for PVESP-1, by immunizing with recombinantly expressed antigen and using the antisera to determine if it recognizes native 70 kD PvESP-2.

Both PvESP-1 and PvESP-2 are successfully expressed in *E. coli* and expression of these proteins in other systems, such as viral systems, other bacterial systems, yeast systems or mammalian cell culture, is also contemplated and is well within the skill of the art. Using such alternate expression systems may be preferred if glycosylation or other post-translational modification is desired.

Purified native or recombinant peptide antigens of the present invention can be used in immunogenic preparation to raise additional antibodies. Such preparations will include immunogenically effective amounts of the present antigens as well as pharmaceutically acceptable vehicles, carriers, buffers, fillers adjuvants and/or diluents.

Peptide antigens of the present invention can be purified by well-known chromatographic techniques. Examples include SDS or native PAGE gel elution, size exclusion gel filtration, anion/cation exchange, antibody affinity, protein binding to immobilized glutathione or MBP fusion partner binding to immobilized amylase, metal binding with a polyhistadine linker peptide after expression in a suitable plasmid vector and cell host, or combinations thereof.

As is evident to one of ordinary skill, it is only certain portions or epitopes of the proteins which are recognized by Mabs. The portions of the protein(s) containing the relevant epitopes can be identified. Fragments of the gene can be subcloned into the appropriate reading frame of a plasmid expression vector and used to transfect *E. coli* (or other host system) and expressed by induction. Defined gene fragments can be generated using restriction enzymes with cutting sites within the gene. Alternatively, appropriate oligonucleotide primers can be used in a PCR-based amplification reaction to engineer the DNA fragment to be subcloned into the plasmid expression vector. Once the expression vector is constructed, the recombinant immunoreactive fragments (or analogs, e.g. as a fusion polypeptide) are expressed. The produced fragments are then reacted with antibodies as above in Western immunoblots, ELISA tests, or other immunochemical assay methods to determine which portion or portions of the protein specifically interact with the antibodies. These methods work well for defining relatively large or small regions of a protein to locate the corresponding epitope and is effective in identifying conformation-dependent (discontinuous) epitopes, or linear epitopes. An alternative method for identifying antigenic determinants is the use of overlapping synthetic peptides of 8–15 amino acids that correspond to the deduced amino acid sequence of the gene. Reactivity of these peptides can be determined using ELISA-based assays, such as the methodology of Geysen et al. (*Journal of Immunological Methods,* 102:259–274, 1987) or using commercial-based peptide synthesis kits, i.e., Pepscan or Inimotope. (Cambridge Research Biochemicals, Valley stream, N.Y. and Chiron, Emeryville, Calif., respectively) This method is especially effective in determination of linear epitopes.

The detection of parasite antigens present in a biological fluid (e.g. plasma), such as PvESP-1 and PvESP-2, can constitute a method for the diagnosis of acute or chronic *P. vivax* malaria infections. To be useful, such an antigen should contain epitopes unique to the *P. vivax* species to allow specific diagnosis and differential diagnosis from other malarial infections, and should preferably be conserved within all or most isolates of that species (more than one antigens can be used to generate antibodies if necessary to accommodate strain variations). Either monoclonal antibodies or polyclonal antibodies could be used in the assay, with monoclonals preferred. The epitopes recognized by the monoclonal antibodies 1D11.G10 (anti-PvESP-1) and 3D4.E2 (anti-PvESP-2) are present in all or most *P. vivax* so far tested (25/26 for 1D11.G10 and 26/26 for 3D4.E2). However, these antigens are not present in *P. falciparum* (FIG. 4A, lane 3), *P. malariae* (lane 2), *P. coatneyi* (lane 4), *P. knowlesi* (lane 5), or *P. berghei* (lane 1). 1D11.G10 does cross-react with *P. cynomolgi* (lane 6), a simian malaria parasite very closely related to *P. vivax* (lane 7), but never found to occur as a naturally acquired human malaria infection. The mAB 3D4.E2 in particular only recognizes *P. vivax* and thus far does so 100% of the time. Of course, any strain differences that may be encountered may be accounted for in an assay by provision of additional appropriate antibodies, or by provision of antibodies directed to interstrain conserved epitopes, which can be conveniently raised against recombinant versions of PvESP-1 and PvESP-2 as well as immunoreactive fragments and analogs thereof.

The detected antigens are relatively stable in vivo; that is, they are not rapidly degraded and/or removed from circulation. PvESP-1 and PvESP-2 can be detected by Western immunoblot in the plasma of squirrel (Saimiri) monkeys experimentally infected with *P. vivax* (FIG. 4A, lane 3) and in the plasma of humans from endemic areas that are infected with *P. vivax* (FIGS. 4C, lanes 8–11 and 4D, lanes 5–7). The antigens are not detected in plasma of individuals infected only with *P. falciparum* (FIGS. 4C, lanes 3–7 and 4D, lanes 6 and 7), the major human malaria parasite that must be differentiated from *P. vivax*. The squirrel monkey model closely approximates what would occur in naturally infected humans, but under more controlled conditions than that of work conducted in the field within endemic areas. In Saimiri monkey infections, the antigen can be detected with the present antibodies when there are 1000 parasites/$\mu$l blood. In humans, early acute infections are detected. Again, as is evident to one of ordinary skill, the isolation of the genes means that high-titer, high-affinity (e.g., of the order of $10^{10}$ liters/mol) antibodies can be produced using standard methodology. These antibodies will be used to increase the sensitivity and specificity of the assay.

Other serological assay formats based on antigen capture and a reporter signal have produced similar results as described above using mABs 3D4.1E2 and 1D11.G10. Based on these successes, it is anticipated that these mAbs or others to be produced using the recombinant proteins or immunogenic fragments thereof can be adapted for use in immunoassay systems (using either labelled Abs or labelled antigens) well-known in the diagnostic testing art.

All well-known methods of labelling antibodies are contemplated, including without limitation enzymatic conjugates, direct labelling with dye, radioisotopes, fluorescence, or particulate labels, such as liposome, latex, polystyrene, and colloid metals or nonmetals. Multiple antibody assay systems, such as antigen capture sandwich assays, are also within the scope of this invention. Further, competitive immunoassays involving labelled protein or assays using the labelled protein to detect serum antibodies are also contemplated forms of the diagnostic assays of the present invention. Beyond diagnostic assays which occur in solution, assays which involve immobilized antibody or protein are also considered within the scope of the invention. (See, for example, Miles et al., *Lancet* 2:492, 1968; Berry et al., *J. Virol. Met.* 34:91–100, 1991; Engvall et al., *G. Immunochemistry,* 8:871, 1971, Tom, *Liposomes and Immunology,* Elsevier/North Holland, New York, N.Y., 1980; Gribnau et al., *J. of Chromatogr.* 376:175-89, 1986 and all references cited therein).

Examples of the types of labels which can be used in the present invention include, but are not limited to, enzymes, radioisotopes, fluorescent compounds, chemiluminescent compounds, bioluminescent compounds, particulates, and metal chelates. Those of ordinary skill in the art will know of other suitable labels for binding to the monoclonal or polyclonal antibody (or to an antigen) or will be able to ascertain the same by the use of outine experimentation. Furthermore, the binding of these labels to the monoclonal or polyclonal antibody (or antigen) can be accomplished using standard techniques commonly known to those of ordinary skill in the art.

One of the ways in which an assay reagent (generally, a monoclonal antibody, polyclonal antibody or antigen) of the present invention can be detectably labeled is by linking the monoclonal antibody, polyclonal antibody, or antigen to an enzyme. This enzyme, in turn, when later exposed to its substrate, will react with the substrate in such a manner as to produce a chemical moiety which can be detected as, for example, by spectrophotometric or fluorometric means.

Examples of enzymes which can be used to detectably label the reagents of the present invention include malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

The presence of the detectably labeled reagent of the present invention can also be detected by labeling the reagent with a radioactive isotope which can then be determined by such means as the use of a gamma counter or a scintillation counter. Isotopes which are particularly useful for the purpose of the present invention are $^{3}$H, $^{125}$I, $^{32}$P, $^{35}$S, $^{14}$C, $^{51}$Cr, $^{36}$Cl, $^{57}$Co, $^{58}$Co, $^{59}$Fe and $^{75}$Se.

It is also possible to detect the binding of the detectably labeled reagent of the present invention by labeling the monoclonal or polyclonal antibody with a fluorescent compound. When the fluoroescently labeled reagent is exposed to light of the proper wave length, its presence can then be detected due to the fluorescence of the dye. Among the most commonly used fluorescent labelling compounds are fluorescein isothiocyanate, rhodamine, phycoerythrin, phycocyanin, allophycocyanin, o-phthaldehyde and fluorescamine.

The reagents according to the invention also can be detectably labeled using fluorescent emitting metals such as $^{152}$Eu, or others of the lanthanide series. These metals can be attached to the reagent molecule using such metal chelating groups as diethylenetriaminepentaacetic acid (DTPA) or ethylenediaminetetraacetic acid (EDTA) and salts thereof.

The reagents of the present invention also can be detectably labeled by coupling it to a chemiluminescent compound. The presence of the chemiluminescent-tagged reagent is then determined by detecting the presence of luminescence that arises during the course of the chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the reagent of the present invention. Bioluminescence is a type of chemiluminescence found in biological systems in which a catalytic protein increases the efficiency of the chemiluminescent reaction. The presence of a bioluminescent reagent is determined by detecting the presence of luminescence. Important bioluminescent compounds for purposes of labeling are luciferin, luciferase and aequorin.

Another technique which may also result in greater sensitivity when used in conjunction with the present invention consists of coupling the monoclonal or polyclonal antibody of the present invention to low molecular weight haptens. The haptens can then be specifically detected by means of a second reaction. For example, it is common to use such haptens as biotin (reacting with avidin) or dinitrophenol, pyridoxal and fluorescamine (reacting with specific antihapten antibodies) in this manner.

Any biological sample containing the detectable yet unknown amount of P. vivax specific blood-stage antigen can be used to assay. Normally, the sample is preferably a liquid, such as, for example, urine, saliva, cerebrospinal fluid, blood, serum and the like, or a solid or semi-solid, such as, for example, tissue, feces and the like.

It appears that 1D11.G10 may recognize a repeated epitope since it has been successfully used in a two-site antigen capture immunoassay using the same mAb for capture and an alkaline phosphatase labelled mAb or mAb conjugated to liposomes encapsulating a marker dye for the reporter antibody (Example 6). Eleven of 15 plasma samples from P. vivax infected individuals were positive by alkaline phosphatase conjugated antibody. Thirteen of 15 samples were positive by liposome conjugated antibody. None of 18 P. falciparum infected plasma samples were positive. Therefore, antibodies to PvESP-1 and PvESP-2 appear quite effective when used in a diagnostic assay of P. vivax infection and further, such assays appear to specifically identify P. vivax infection. It is anticipated that assays based on mAb specific for particular epitopes and selected for their high titer and/or affinity will serve to increase the specificity and sensitivity of the assay.

In general, increases in sensitivity are a development consideration and are achieved by optimization of all reagents, including the concentrations conjugated to reporter systems, adsorbed to solid phase surfaces, specificity of the Abs, and affinity of the Abs. These steps are routinely done and evaluated during assay development and are well within the skill of those working in the art.

As is evident to one of ordinary skill, the diagnostic assay of the present invention includes kit forms of such an assay. This kit would include anti-PvESP-1 and/or anti-PvESP-2 monoclonal or polyclonal antibodies (raised against whole PvESP or immunoreactive fragments or analogs thereof) which can be optionally immobilized, as well as any necessary reagents and equipment to prepare the biological sample for and to conduct analysis, e.g. preservatives, reaction media such as nontoxic buffers, microtiter plates, micropipettes, etc. The reagent (Abs and/or antigens) can be lyophilized or cryopreserved. As described above, depending on the assay format, the antibodies can be labelled, or the kit can further comprise labelled PvESP-1 or PvESP-2 protein or fragments or analogs thereof containing the relevant epitopes.

The types of immunoassays which can be incorporated in kit form are many. Typical examples of some of the immunoassays which can utilize the antibodies of the invention are radioimmunoassays (RIA) and immunometric, or sandwich, immunoassays.

"Immunometric assay" or "sandwich immunoassay", includes simultaneous sandwich, forward sandwich and reverse sandwich immunoassays. These terms are well understood by those skilled in the art. Those of skill will also appreciate that the monoclonal antibodies, polyclonal antibodies and/or antigens of the present invention will be useful in other variations and forms of immunoassays which are presently known or which may be developed in the future. These are intended to be included within the scope of the present invention.

In a forward sandwich immunoassay, a sample is first incubated with a solid phase immunoadsorbent containing monoclonal or polyclonal antibody(ies) against the antigen. Incubation is continued for a period of time sufficient to allow the antigen in the sample to bind to the immobilized antibody in the solid phase. After the first incubation, the solid phase immunoadsorbent is separated from the incubation mixture and washed to remove excess antigen and other interfering substances, such as non-specific binding proteins, which also may be present in the sample. Solid phase immunoadsorbent containing antigen bound to the immobilized antibody is subsequently incubated for a second time with soluble labeled antibody or antibodies. After the second incubation, another wash is performed to remove unbound labeled antibody(ies) from the solid phase immunoadsorbent and removing non-specifically bound labeled antibody(ies). Labeled antibody(ies) bound to the solid phase immunoadsorbent is then detected and the amount of labeled antibody detected serves as a direct measure of the amount of antigen present in the original sample.

Alternatively, labeled antibody which is not associated with the immunoadsorbent complex can also be detected, in which case the measure is in inverse proportion to the amount of antigen present in the sample. Forward sandwich assays are described, for example, in U.S. Pat. Nos. 3,867,517; 4,012,294 and 4,376,110.

In carrying out forward immunometric assays, the process may comprise, in more detail: (a) first forming a mixture of the sample with the solid phase bound antibody(ies) and incubating the mixture for a time and under conditions sufficient to allow antigen in the sample to bind to the solid phase bound antibody(ies), (b) adding to the mixture after said incubation of step (a) the detectably labeled antibody or antibodies and incubating the new resulting mixture for a time and under conditions sufficient to allow the labeled antibody to bind to the antigen-antibody complex on the solid phase immunoadsorbent; (c) separating the solid phase immunoadsorbent from the mixture after the incubation in step (b); and (d) detecting either the labeled antibody or antibodies bound to the antigen-antibody complex on the solid phase immunoadsorbent or detecting the antibody not associated therewith.

In a reverse sandwich assay, the sample is initially incubated with labeled antibody(ies), after which the solid phase immunoadsorbent containing multiple immobilized antibodies is added thereto, and a second incubation is carried out. The initial washing step of a forward sandwich assay is not required, although a wash is performed after the second incubation. Reverse sandwich assays have been described, for example, in U.S. Pat. Nos. 4,098,876 and 4,376,110.

In carrying out reverse immunometric assays, the process may comprise, in more detail; (a) first forming a mixture of the sample with the soluble detectably labeled antibody for a time and under conditions sufficient to allow antigen in the sample to bind to the labeled antibody; (b) adding to the mixture after the incubation of step (a) the solid phase bound antibodies and incubating the new resulting mixture for a time and under conditions sufficient to allow antigen bound to the labeled antibody to bind to the solid phase antibodies; (c) separating the solid phase immunoadsorbent from the incubating mixture after the incubation in step (b); and (d) detecting either the labeled antibody bound to the solid phase immunoadsorbent or detecting the labeled antibody not associated therewith.

In a simultaneous sandwich assay, the sample, the immunoadsorbent having multiple immobilized antibodies thereon and labeled soluble antibody or antibodies are incubated simultaneously in one incubation step. The simultaneous assay requires only a single incubation and does not include washing steps. The use of a simultaneous assay is by far the preferred one. This type of assay brings about ease of handling, homogeneity, reproducibility, and linearity of the assays and high precision. The sample containing antigen, solid phase immunoadsorbent with immobilized antibodies and labeled soluble antibody or antibodies is incubated under conditions and for a period of time sufficient to allow antigen to bind to the immobilized antibodies and to the soluble antibody(ies). In general, it is desirable to provide incubation conditions sufficient to bind as much antigen as possible, since this maximizes the binding of labeled antibody to the solid phase, thereby increasing the signal. Typical conditions of time and temperature are two hours at 45° C., or twelve hours at 37° C. Antigen typically binds to labeled antibody more rapidly than to immobilized antibody, since the former is in solution whereas the latter is bound to the solid phase support. Because of this, labeled antibody may be employed in a lower concentration than immobilized antibody, and it is also preferable to employ a high specific activity for labeled antibody. For example, labeled antibody might be employed at a concentration of about 1–50 ng per assay, whereas immobilized antibody might have a concentration of 10–500 ng per assay per antibody. The labeled antibody might have a specific activity with, for instance, one radioiodine per molecule, or as high as two or more radioiodines per molecule of antibody.

Of course, the specific concentrations of labeled and immobilized antibodies, the temperature and time of incubation as well as other assay conditions can be varied, depending on various factors including the concentration of antigen in the sample, the nature of the sample and the like. Those skilled in the art will be able to determine operative and optimal assay conditions for each determination by employing routine experimentation.

After the single incubation period, the solid phase immunoadsorbent is removed from the incubation mixture. This can be accomplished by any of the known separation techniques, such as sedimentation and centrifugation. A washing step is not required prior to detection of bound labeled antibody. Detection can be performed by a scintillation counter, for example, if the label is a radioactive gamma-emitter, or by a fluorometer, for example, if the label is a fluorescent material. In the case of an enzyme label, the detection can be done by calorimetric methods employing a substrate for the enzyme.

In carrying out the simultaneous immunometric assay on a sample containing a multivalent antigen, the process may comprise, in more detail:

(a) simultaneously forming a mixture comprising the sample, together with the solid phase bound antibody and the soluble labeled antibody or antibodies;

(b) incubating the mixture formed in step (a) for a time and under conditions sufficient to allow antigen in the sample to bind to both immobilized and labeled antibodies;

(c) separating the solid phase immunoadsorbent from the incubation mixture after the incubation; and (d) detecting either labeled antibody bound to the solid phase immunoadsorbent or detecting labeled antibody not associated therewith.

Other such steps as washing, stirring, shaking filtering and the like may of course be added to the assays, as is the custom or necessity for any particular situation.

In the preferred mode for preforming the assays it is important that certain "blockers" be present in the incubation medium (usually added with the labeled soluble antibody). The "blockers" are added to assure that non-specific proteins, protease, or human antibodies to mouse immunoglobulins present in the experimental sample do not cross-link or destroy the monoclonal or polyclonal antibodies on the solid phase support, or the radiolabeled indicator antibody, to yield false positive or false negative results. The selection of "blockers" therefore adds substantially to the specificity of the assays described in the present invention.

It has been found that a number of nonrelevant (i.e., nonspecific) monoclonal or polyclonal antibodies of the same class or subclass (isotype) as those used in the assays (e.g., IgG1, IgG 2a2, IgM, etc.) can be used as "blockers". The concentration of the "blockers" (normally 1–100, $\mu g/\mu l$) is important, in order to maintain the proper sensitivity yet inhibit any unwanted interference by mutually occurring cross reactive proteins in human serum. In addition, the buffer system containing the "blockers" needs to be optimized. Preferred buffers are those based on weak organic acids, such as imidazole, HEPPS, MOPS, TES, ADA, ACES, HEPES, PIPES, TRIS, and the like, at physiological pH ranges. Somewhat less preferred buffers are inorganic buffers such as phosphate, borate or carbonate. Finally, known protease inhibitors should be added (normally at 0.01–10 microns/ml) to the buffer which contains the "blockers".

There are many solid phase immunoadsorbents which have been employed and which can be used in the present invention. Well-known immunoadsorbents include nitrocellulose, glass, polystyrene, polypropylene, dextran, nylon and other materials; tubes, beads, and microtiter plates formed from or coated with such materials, and the like. The immobilized antibodies can be either covalently or physically bound to the solid phase immunoadsorbent, by techniques such as covalent bonding via an amide or ester linkage, or by absorption. Those skilled in the art will know many other suitable solid phase immunoadsorbents and methods for immobilizing antibodies thereon, or will be able to ascertain such, using no more than routine experimentation.

Details of the operation and practice of the present invention are set forth in the specific examples which follow. However, these examples are not to be interpreted as limiting the scope of the present invention.

EXAMPLE 1

Method of Making the Monoclonal Antibodies Specific for PvESP-1 and PvESP-2

Balb/c mice were immunized intraperitoneally with $5 \times 10^8$ purified *P. vivax* (of the Belem strain infected red blood cells (IRBC) in complete Freud's adjuvant. Immunization was repeated at 2 and 7 weeks using incomplete Freud's adjuvant and finally at 14 weeks without adjuvant. 3 days later, spleen cells from the immunized mouse were fused with myeloma cell line NY-FOX (Hyclone, Utah; Taggart, *Science, 219:1228–1230, 1983*) according to the basic method of Galfre et al. (*Nature*, 266:550–552, 1977). Cells were plated directly into microtiter wells and cultured (Rener et al., *Proc. Natl. Acad. Sci. USA*, 77:6797–6799, 1980) such that 1 to 2 weeks later, 1 or more hybrid colonies were observed in all wells. Culture supernatants were collected and screened by immunofluorescence assay using smears of *P. vivax* infected blood that also contained normal red blood cells. Those cells producing antibodies which selectively reacted with IRBCs were expanded and cryopreserved. Secondary screening was performed by SDS-PAGE with hybridoma culture supernatants from expanded cultures that had been obtained by centrifugation. Those mAbs which reacted with *P. vivax* blood stage extracts and culture supernatants (prepared essentiailly as described in Galinski et al., *Cell*, 69:1213–1226, 1992) were selected for further study. Three such mAbs are designated 1D11.G10, 3D4.A2, and 1A3.B4.

EXAMPLE 2

Screening of *P. vivax* λZAPII Expression Library with the mAbs

*P. vivax* genomic DNA was isolated and digested with mung bean nuclease (U.S. Biochemical) following the procedures of Vernick et al. (*Nucl. Acids Res.*, 16:6883–6896, 1988) and as modified by Galinski et al. (supra) Specifically, the DNA was digested with 42.5–45% formamide. The digested DNA was ligated into the λZAPII vector (Stratagene, LaJolla, Calif.) and the resulting phage were used to infect *E. coli*. Expression was induced by growth on IPTG (isopropylthio-β-D-galactoside) containing nitrocellulose plates overlaying the agar plates, and the resulting plaques were screened with the mAbs using standard immuno-detection methods (see, for example, Maniatis, *Molecular Cloning: A Laboratory Manual*, 2nd ed., Chapter 12, 1989).

After screening approximately $3 \times 10^5$ recombinant plaques, mAb 1D11.G10 specifically recognized one recombinant phage plaque. This phage clone, PvMB3.3.1 was purified, and in vivo excised with the aid of helper phage R408 (Stratagene, LaJolla, Calif.) to yield the clone as a pBluescript plasmid retaining the recombinant DNA as a 3.34 kb insert (Short et al., *Nucleic Acids Res.*, 16:7583, 1988).

After screening approximately $4 \times 10^5$ plaques, mAb 3D4.E2 also revealed one phage plaque recognized by the antibody. This clone, PvMB2.5.1 was plaque purified and in vivo excised, as above, to yield a pBluescript plasmid containing the 3.7 kb DNA insert.

EXAMPLE 3

Expression of the Cloned Proteins in *E. coli*

The isolated pBluescript plasmids where transformed into *E. coli* and expression was induced by growth in the presence of IPTG using standard methodology (Maniatis, *Molecular Cloning: A Laboratory Manual*, 2nd ed., Chapter 1, 1989). Proteins produced by the cultures were isolated, separated on a gel, blotted and probed using standard techniques (Maniatis, *Molecular Cloning: A Laboratory Manual*, 2nd ed., Chapter 18, 1989). Probing the blot of PvMB3.3.1 with 1D11.G10 revealed multiple bands, the largest of which was 205–210 kD. Probing the blot of PvMB2.5.1 revealed a 60 kD band. These results indicate that the cloned inserts encode the epitopes recognized by these mAbs.

EXAMPLE 4

Sequencing of the Pv3.3.1 Insert

The insert was directly sequenced from the pBluescript excision plasmid. Nested deletions of 100–300 bp intervals were created using exonuclease III and mung bean nuclease (U.S. Biochemical, Cleveland, Ohio) and standard methodology. DNA sequences were generated using the dideoxy termination method sequencing methodology (Sanger et al., *Proc. Natl. Acad. Sci. USA*, 74:5463–5467, 1977). The entire PvESP-1 gene was sequenced on both DNA strands, and is SEQ ID No: 1. The deduced protein sequence (SEQ ID No: 2) was analyzed using Pustell and MacVector software programs (IBI). GenBank (release 70) and the Swiss Protein Data Bank (release 20) were screened for DNA and protein sequence homologies using the GCG Sequence Analysis Software Package, Version 7.0 (Genetics Computer Group, Inc.).

EXAMPLE 5

Cross-reactivity Test with Other Plasmodium Species

FIG. 4A was produced as follows. *P. vivax* trophozoite-infected erythrocytes ($2 \times 10^4$), 25 µl of supernatants from *P. vivax* trophozoite and rupturing schizont-infected red blood cell cultures, and 20 µl of a 1:10 dilution of *P. vivax* infected Saimiri monkey plasma were mixed with sample buffer and electro-phoresed on an SDS-PAGE gel. The gel was electrophoretically transferred to 0.2 µm nitrocellulose (NC) by Western blot (Towbin, H. et al., *Proc. Natl. Acad. Sci. USA*, 76:4350, 1979). The NC was blocked with 3% non-fat dry milk and probed with mAb 1D11.G10 at 2 mg/ml in TBS. The blot was washed with TBS/0.05. tween 20 and reprobed with alkaline phosphatase conjugated anti-mouse IgG (Promega, Madison, Wis.) and developed with P-nitroblue tetrazolium chloride/5-bromo-4-chloro-3 indolyl phosphate (U.S. Biochemicals, Cleveland, Ohio).

FIG. 4B. was produced as follows. *P. vivax* IRBC were acquired from infected Saimiri monkey, *P. cynomolgi* (M strain) IRBC was from infected Rhesus monkeys, *P. knowlesi* IRBC were Saimiri monkey, *P. coatneyi* IRBC were from Rhesus monkeys, *P. falciparum* from human rbc in in vitro culture, *P. malariae* from infected Aotus monkeys, and *P. berghei* from infected rats. SDS-PAGE and nitrocellulose transfer were done as above with $1 \times 10^5$ parasites/lane dissolved in SDS-PAGE sample buffer. Indirect immunofluorescence assay was performed by making smears of IRBC on slides and reacting 1D11.G10 or 3D4.E2 with smears and using FITC conjugated goat anti-mouse IgG as secondary antibody with the same results as Western blot.

These results show that there is no cross-reactivity with other malarial species.

EXAMPLE 6

Diagnostic Assay Using Alkaline Phosphatase and Liposome Conjugated mAb

Unlabelled mAb is absorbed to nitrocellulose sheets (5 µm average pore size) at 5 mg Ab/ml in PBS. The sheet is washed and blocked with 3% non-fat dry milk in TBS. The sheet is layered on an ELISA apparatus (Pierce) and a 96-well plexiglass top (like a slot blot apparatus) is secured in place over the nitrocellulose sheet. Diluted plasma (1:10–100 µl) samples are applied to the wells and drawn through the nitrocellulose by vacuum. The wells are washed by vacuum and mAb 1D11.G10 conjugated to alkaline phosphatase is applied to the wells. Alkaline phosphatase conjugation was accomplished by the glutaraldehyde method of Avrameas (*Immunochemistry*, 6:43, 1967). The alkaline phosphatase conjugated mAb is pulled through the nitrocellulose by vacuum, the wells are washed, and then the developer substrates NBT-BCIP are added to and pulled through the wells. Positive reactions are assessed by the appearance of a purple-violet to blue-black precipitate forming in the wells at the surface of the nitrocellulose. Eleven of the 15 plasma samples from *P. vivax* individuals were positive using the alkaline phosphatase conjugated mAb 1D11.G10. All samples were assessed for infection with *P. vivax, P. falciparum*, or both, by Giemsa-stained thick films of blood samples. False positives thus, would show a positive reaction, but would be negative for *P. vivax* parasites in thick films. No such reactions were seen.

The liposome-based test was similar to the alkaline phosphatase-based test. As in the alkaline phosphatase assay, the secondary (reporter) mAb was conjugated to liposomes that contained a bright red to maroon dye. Thus, the appearance of red on the nitrocellulose was the reporter system and an enzymatic development step is not needed as in the alkaline phosphatase system. Thirteen of 15 infected samples were positive using the liposome conjugated 1D11.G10. This assay can also be adapted to a strip test where a mAb or polyclonal Ab is absorbed to a NC strip that overlays an absorbent pad. Then, test plasma, antibody conjugated liposomes, and washing solutions are wicked upwards by diffusion and a positive test is indicated by a red-to-magenta line across the NC strip assay.

EXAMPLE 7

Competitive Diagnostic Test for Malaria Which Indicates Specific Infection with *P. vivax*

In a calorimetric immunoassay for PvESP-1 and/or PVESP-2, large, unilamellar phospholipid vesicles approximately 0.2 micrometers in diameter are loaded with high concentrations of Sulforhodamine B or a similar dye. The PvESP-1 and/or PvESP-2 is coupled to phosphatidylethanolamine or another component of the lipid vesicle, and incorporated into the lipid formulation, thus conferring immunological specificity. Methods of formation of the vesicles, loading the vesicles, and coupling the protein to the phosphatidylethanolamine are disclosed in O'Connell et al. (*Clin. Chem*, 31:1424–1426). The liposomes are then used as tracers in simple competitive-binding immunoassays with antibody-coated tubes. The results are read spectrophotometrically. Specific immunoassay methods are described in O'Connell et al., supra, as well as O'Connell, MG and DI, December, 1985, pp. 31–36. As this is a competitive assay, the less signal seen, the more PvESP-1 and/or PvESP-2 will be present in the sample. It is anticipated that this assay will be selective for *P. vivax* infection, given the selectivity of the antibodies 1D11.G10, 3D4.A2, and 1A3.B4 as shown in Example 5.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 3337 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmodium vivax ( v i i ) IMMEDIATE SOURCE:
        ( B ) CLONE: PvMB3.3.1

( x i ) SEQUENCE DESCRIPTION: SEQ ID NO:1:

```
GAATTCCGGT  AAAGTAACAA  CTATGGTTTC  GTATCTATAT  ATAACCTTAC  TAATTTTATC      60

TTTTGCTTTT  CTTTTAATTC  ATGCTTCAAC  AGTAAGATAA  AAATAATCTA  TAAAAACTGC     120

TATATATACA  TATATATTCA  TAAGTGGCAT  TTGTGAATTG  CGATCATTTA  AATTTACGTA     180

AAAACAATAT  TGAAAAAAAT  TTTTTTTTTT  TTTTTTTTTT  TGTTCTACAG  AACGATTTAG     240

AATTGGAAAA  TGCTTCTGAT  GATGTTGTAG  AGGTGGAGGA  TCCTTCAAAC  GACGGTTTAG     300
```

-continued

| | | | | | |
|---|---|---|---|---|---|
| AATTAGAAGA | GGAAAATTTT | GATGAGAATT | CAGGTGATGA | TGAAACTCTT | TTAGATGCTA | 360 |
| CCCCCGAAGA | TGACTTTGCC | TTAACAGATT | TGCCAATTGA | AGACGATGAG | GAAGTCAACG | 420 |
| AAACGTTAGA | TGGAGGTGAA | TCATTAGGAG | AGGTTTCCAC | TGAAGATATG | GAAACAGAAG | 480 |
| ATGGCTCAAC | AGATGATACG | GAAACAGAAG | AAGGACTACC | TGGTGATATG | GAAGGAGAAG | 540 |
| AAGAAGCTGG | CGATATGGAA | GCAGGGGAAG | AAGCTGGTGA | TTTGGAAGCA | GGGGAAGAAA | 600 |
| CTGGCGATTT | GGAAGCAGGG | GAAGAAACTG | GCGATTTGGA | AGCAGGGGAA | GAAGCTGGTG | 660 |
| ATTTGGAAGC | AGGGGAAGAA | ACTGGCGATT | GGAAGCAGG | GAAGAAACT | GGAGATGCGG | 720 |
| AAACTGAAGA | AGGAGCAACT | GGAGATGCGG | AAACTGAAAA | TGGAGCAACT | GTGTATGTAG | 780 |
| ACACAGAAGA | TAGTTCAGCT | GATGGAGCAG | AAAAAGTACA | TGTTCCTGCT | CAAGAAAATG | 840 |
| TACAACCTGC | CGATAGTAAT | GATGCCCTCT | TTGGAAGTAT | TTTGGATAAA | GATATAATTT | 900 |
| TTGATCATAT | TAAAGATTTC | GAGCCACTAT | TCGAACAAAT | TGTGGCGGGT | ACTGCTAAAC | 960 |
| ATGTTACGGG | ACAAGAATTG | CCAATGAAAC | CTGTACCATT | ACCAGTGGCA | GAAGAGCCCG | 1020 |
| CGCAAGTACC | AGCGGAAGAA | TTAGATGCCA | CTCCAGAGGA | TGACTTCGCA | TTAGATGTTA | 1080 |
| CAGAATCTCC | CGAGGAAGTA | GAATTAGTAT | TAGATGAAGA | GGCAACTGAA | GAAGAATCAA | 1140 |
| CGGAAGTGGG | ACCAACGGAA | GAAGGACCAA | CCGAAGAATT | AGATGCCACT | CCAGAGGATG | 1200 |
| GATTTCGCAT | TAGACGAAAC | TGCAGAAGGA | GAAACAGAAG | AAACGTAGAG | GGAGAAGAAA | 1260 |
| CAGAAGAAGC | TGCAGAAGGA | GAAGTATCAG | AAGAAACTCC | AGAAGGAGAA | GAAGAGTTAG | 1320 |
| AGGCAACTCC | AGAGGATGAT | TTCGCATTAG | ATGGAACTAC | ATTAGAAGAA | ACCGAAGAAA | 1380 |
| CTGCAGAAGG | AGAAGAAACC | GTAGAGGGAG | AAGAAACCGT | AGAGGGAGAA | GAAACCGTAG | 1440 |
| AGGGAGAAGA | AGCTGCAGAA | GGAGAAGAAG | AGTTAGAGGC | AACTCCAGAG | GATGACTTCC | 1500 |
| AATTAGAAGA | ACCATCAGGA | GAAGGAGAAG | GGAAGGAGA | AGGAGAAGGG | GAAGGAGAAG | 1560 |
| GAGAAGCGTT | AGTAGCAGTG | CCAGTAGTGG | CCGAACCGGT | AGAAGTAGTG | ACTCCTGCTC | 1620 |
| AGCCTGTCAA | ACCAATGGTC | GCTCCAACGG | CAGATGAAAC | TTTATTCGTT | GATATCTTAG | 1680 |
| ATAACGATTT | AACGTATGCA | GACATTACAT | CCTTTGAGCC | ATTATTTAAA | CAAATCCTCA | 1740 |
| AGGATCCTGA | TGCAGGAGAG | GCTGTAACAG | TACCATCAAA | GGAAGCACCT | GTACAAGTAC | 1800 |
| CAGTGGCAGT | AGGGCCCGCG | CAAGAAGTGC | CAACGGAAGA | ATTGATGCAA | CTCCAAGAGG | 1860 |
| ACGATTTCGA | ATTAGAAGGA | ACTGCAGAAG | CTCCAGAGGA | AGGAGAATTA | GTATTAGAAG | 1920 |
| GAGAAGGAGA | ACCAACGGAA | GAAGAGCCAA | GAGAAGGAGA | GCCAACAGAA | GGAGAAGTGC | 1980 |
| CAGAAGAAGA | ATTAGAGGCA | ACTCCAGAGG | ACGATTTCGA | ATTAGAAGAA | CCAACAGGAG | 2040 |
| AAGAAGTAGA | AGAAACCGTA | GAGGGCGAAG | AAACTGCAGA | AGGAGAAGAA | GTGGAAGAGG | 2100 |
| TACCTGCAGA | AGTAGAAGAA | GTGGAAGAGG | TACCTGCAGA | AGTAGAAGAA | GTGGAAGAGG | 2160 |
| TACCAGAAGA | AGTAGAAGAG | GTACCCGCAG | AAGTAGAAGA | AGTGGAAGAG | GTACCAGAAG | 2220 |
| AAGTGGAAGA | GGTACCAGAA | GAAGTGGAAG | AGGTACCAGA | AGAAGTGGAA | GAGGTACCAG | 2280 |
| AAGAAGTGGA | AGAAGTGGAA | GAAGTAGAAG | AAGTAGAGGT | ACCAGCGGTA | GTAGAAGTAG | 2340 |
| AAGTACCAGC | GGTAGTAGAA | GAAGAGGTGC | CAGAAGAAGT | AGAAGAAGAA | GAAGAAGAGG | 2400 |
| AAGAACCAGT | AGAGGAAGAA | GATGTATTAC | AATTAGTAAT | ACCATCGGAA | GAAGATATAC | 2460 |
| AATTAGACAA | ACCAAAGAAA | GACGAATTAG | GCTCTGGAAT | TTTATCTATC | ATCGACATGC | 2520 |
| ACTACCAAGA | CGTTCCAAAG | GAATTTATGG | AAGAAGAAGA | AGAAACTGCA | GTGTATCCAT | 2580 |
| TGAAACCAGA | AGATTTTGCA | AAGGAAGATT | CACAATCTAC | AGAATGGCTC | ACATTCATTC | 2640 |
| AAGGCCTAGA | AGGCGACTGG | GAACGATTAG | AAGTGAGCTT | AAATAAGGCT | AGAGAAAGAT | 2700 |

```
GGATGGAACA  AAGAAATAAA  GAATGGGCTG  GCTGGCTTCG  CTTAATTGAA  AATAAATGGT    2760

CAGAATATAG  TCAAATTTCA  ACAAAAGGAA  AGGACCCAGC  TGGTTTGAGA  AAACGAGAGT    2820

GGAGCGACGA  GAAATGGAAA  AAATGGTTTA  AAGCAGAAGT  CAAATCCCAA  ATTGATTCAC    2880

ACTTGAAAAA  ATGGATGAAC  GACACTCATT  CCAATTTATT  TAAAATTCTT  GTGAAAGATA    2940

TGTCACAATT  TGAAAACAAG  AAAACCAAAG  AATGGTTAAT  GAATCACTGG  AAAAAGAACG    3000

AACGGGGTTA  TGGTTCTGAA  TCATTTGAAG  TTATGACCAC  ATCAAAATTA  TTAAATGTGG    3060

CTAAGAGTCG  AGAATGGTAC  CGTGCCAATC  CTAATATAAA  TAGAGAAAGA  AGAGAACTCA    3120

TGAAATGGTT  TCTCCTAAAA  GAAAACGAAT  ATTTAGGACA  AAGAATGGAA  AAAATGGACT    3180

CATTGGAAAA  AAGTTAAATT  TTTTGTGTTC  AATTCAATGT  GTACAACATT  TTCTGGAAAA    3240

CGCCTAACCA  AGGAAGAATG  GAATCAATTT  GTTAATGAAA  TAAAAGTTTG  AATTATAGAA    3300

AAAAGAACAG  ATTATTCTCT  TATAAAATAA  ATAATTC                              3337
```

(2) INFORMATION FOR SEQ ID NO:2:

(i) SEQUENCE CHARACTERISTICS:
        (A) LENGTH: 1018 amino acids
        (B) TYPE: amino acid
        (D) TOPOLOGY: linear (ii) MOLECULE TYPE: protein (iii) HYPOTHETICAL: YES (iv) ANTI-SENSE: NO (v) FRAGMENT TYPE: C-terminal (vi) ORIGINAL SOURCE:
        (A) ORGANISM: Plasmodium vivax (vii) IMMEDIATE SOURCE:
        (B) CLONE: PvMB3.3.1

(xi) SEQUENCE DESCRIPTION: SEQ ID NO:2:

```
Asn  Ser  Gly  Lys  Val  Thr  Thr  Met  Val  Ser  Tyr  Leu  Tyr  Ile  Thr  Leu
 1              5                        10                       15

Leu  Ile  Leu  Ser  Phe  Ala  Phe  Leu  Leu  Ile  His  Ala  Ser  Thr  Asn  Asp
              20                        25                       30

Leu  Glu  Leu  Glu  Asn  Ala  Ser  Asp  Asp  Val  Val  Glu  Val  Glu  Asp  Pro
         35                        40                       45

Ser  Asn  Asp  Gly  Leu  Glu  Leu  Glu  Glu  Glu  Asn  Phe  Asp  Glu  Asn  Ser
     50                        55                       60

Gly  Asp  Asp  Glu  Thr  Leu  Leu  Asp  Ala  Thr  Pro  Glu  Asp  Asp  Phe  Ala
 65                       70                       75                       80

Leu  Thr  Asp  Leu  Pro  Ile  Glu  Asp  Asp  Glu  Val  Asn  Glu  Thr  Leu
                   85                       90                       95

Asp  Gly  Gly  Glu  Ser  Leu  Gly  Glu  Val  Ser  Thr  Glu  Asp  Met  Glu  Thr
                  100                      105                     110

Glu  Asp  Gly  Ser  Thr  Asp  Asp  Thr  Glu  Thr  Glu  Glu  Gly  Leu  Pro  Gly
              115                      120                     125

Asp  Met  Glu  Gly  Glu  Glu  Glu  Ala  Gly  Asp  Met  Glu  Ala  Gly  Glu  Glu
         130                      135                     140

Ala  Gly  Asp  Leu  Glu  Ala  Gly  Glu  Glu  Thr  Gly  Asp  Leu  Glu  Ala  Gly
145                      150                      155                     160

Glu  Glu  Thr  Gly  Asp  Leu  Glu  Ala  Gly  Glu  Glu  Ala  Gly  Asp  Leu  Glu
                  165                      170                     175
```

```
Ala Gly Glu Glu Thr Gly Asp Leu Glu Ala Gly Glu Glu Thr Gly Asp
        180                 185                 190
Ala Glu Thr Glu Glu Gly Ala Thr Gly Asp Ala Glu Thr Glu Asn Gly
        195                 200                 205
Ala Thr Val Tyr Val Asp Thr Glu Asp Ser Ser Ala Asp Gly Ala Glu
        210                 215                 220
Lys Val His Val Pro Ala Gln Glu Asn Val Gln Pro Ala Asp Ser Asn
225                 230                 235                 240
Asp Ala Leu Phe Gly Ser Ile Leu Asp Lys Asp Ile Ile Phe Asp His
                245                 250                 255
Ile Lys Asp Phe Glu Pro Leu Phe Glu Gln Ile Val Ala Gly Thr Ala
                260                 265                 270
Lys His Val Thr Gly Gln Glu Leu Pro Met Lys Pro Val Pro Leu Pro
            275                 280                 285
Val Ala Glu Glu Pro Ala Gln Val Pro Ala Glu Glu Leu Asp Ala Thr
        290                 295                 300
Pro Glu Asp Asp Phe Ala Leu Asp Val Thr Glu Ser Pro Glu Glu Val
305                 310                 315                 320
Glu Leu Val Leu Asp Glu Glu Ala Thr Glu Glu Ser Thr Glu Val
                325                 330                 335
Gly Pro Thr Glu Glu Gly Pro Thr Glu Glu Leu Asp Ala Thr Pro Glu
            340                 345                 350
Asp Gly Phe Arg Ile Arg Arg Asn Cys Arg Arg Arg Asn Arg Arg Asn
            355                 360                 365
Val Glu Gly Glu Glu Thr Glu Ala Ala Glu Gly Glu Val Ser Glu
    370                 375                 380
Glu Thr Pro Glu Gly Glu Glu Leu Glu Ala Thr Pro Glu Asp Asp
385                 390                 395                 400
Phe Ala Leu Asp Gly Thr Thr Leu Glu Glu Thr Glu Glu Thr Ala Glu
                405                 410                 415
Gly Glu Glu Thr Val Gly Glu Glu Thr Val Glu Gly Glu Glu Thr
                420                 425                 430
Val Glu Gly Glu Ala Ala Glu Gly Glu Glu Glu Leu Glu Ala Thr
            435                 440                 445
Pro Glu Asp Asp Phe Gln Leu Glu Glu Pro Ser Gly Glu Gly Glu Gly
    450                 455                 460
Glu Gly Glu Gly Glu Gly Glu Gly Glu Gly Glu Ala Leu Val Ala Val
465                 470                 475                 480
Pro Val Val Ala Glu Pro Val Glu Val Thr Pro Ala Gln Pro Val
                485                 490                 495
Lys Pro Met Val Ala Pro Thr Ala Asp Glu Thr Leu Phe Val Asp Ile
            500                 505                 510
Leu Asp Asn Asp Leu Thr Tyr Ala Asp Ile Thr Ser Phe Glu Pro Leu
            515                 520                 525
Phe Lys Gln Ile Leu Lys Asp Pro Asp Ala Gly Glu Ala Val Thr Val
    530                 535                 540
Pro Ser Lys Glu Ala Pro Val Gln Val Pro Val Ala Val Gly Pro Ala
545                 550                 555                 560
Gln Glu Val Pro Thr Glu Glu Leu Met Gln Leu Gln Glu Asp Asp Phe
                565                 570                 575
Glu Leu Glu Gly Thr Ala Glu Ala Pro Glu Gly Glu Leu Val Leu
                580                 585                 590
Glu Gly Glu Gly Glu Pro Thr Glu Glu Pro Arg Glu Gly Glu Pro
    595                 600                 605
```

-continued

```
Thr Glu Gly Glu Val Pro Glu Glu Leu Glu Ala Thr Pro Glu Asp
    610                 615                 620
Asp Phe Glu Leu Glu Glu Pro Thr Gly Glu Glu Val Glu Glu Thr Val
625                 630                 635                 640
Glu Gly Glu Glu Thr Ala Glu Gly Glu Glu Val Glu Glu Val Pro Ala
                    645                 650                 655
Glu Val Glu Glu Val Glu Glu Val Pro Ala Glu Val Glu Glu Val Glu
                660                 665                 670
Glu Val Pro Glu Glu Val Glu Glu Val Pro Ala Glu Val Glu Glu Val
            675                 680                 685
Glu Glu Val Pro Glu Glu Val Glu Glu Val Pro Glu Glu Val Glu Glu
        690                 695                 700
Val Pro Glu Glu Val Glu Glu Val Pro Glu Glu Val Glu Glu Val Glu
705                 710                 715                 720
Glu Val Glu Glu Val Glu Val Pro Ala Val Val Glu Val Glu Val Pro
                725                 730                 735
Ala Val Val Glu Glu Glu Val Pro Glu Glu Val Glu Glu Glu Glu Glu
                740                 745                 750
Glu Glu Glu Pro Val Glu Glu Glu Asp Val Leu Gln Leu Val Ile Pro
            755                 760                 765
Ser Glu Glu Asp Ile Gln Leu Asp Lys Pro Lys Lys Asp Glu Leu Gly
    770                 775                 780
Ser Gly Ile Leu Ser Ile Ile Asp Met His Tyr Gln Asp Val Pro Lys
785                 790                 795                 800
Glu Phe Met Glu Glu Glu Glu Glu Thr Ala Val Tyr Pro Leu Lys Pro
                805                 810                 815
Glu Asp Phe Ala Lys Glu Asp Ser Gln Ser Thr Glu Trp Leu Thr Phe
                820                 825                 830
Ile Gln Gly Leu Glu Gly Asp Trp Glu Arg Leu Glu Val Ser Leu Asn
            835                 840                 845
Lys Ala Arg Glu Arg Trp Met Glu Gln Arg Asn Lys Glu Trp Ala Gly
    850                 855                 860
Trp Leu Arg Leu Ile Glu Asn Lys Trp Ser Glu Tyr Ser Gln Ile Ser
865                 870                 875                 880
Thr Lys Gly Lys Asp Pro Ala Gly Leu Arg Lys Arg Glu Trp Ser Asp
                885                 890                 895
Glu Lys Trp Lys Lys Trp Phe Lys Ala Glu Val Lys Ser Gln Ile Asp
                900                 905                 910
Ser His Leu Lys Lys Trp Met Asn Asp Thr His Ser Asn Leu Phe Lys
            915                 920                 925
Ile Leu Val Lys Asp Met Ser Gln Phe Glu Asn Lys Lys Thr Lys Glu
    930                 935                 940
Trp Leu Met Asn His Trp Lys Lys Asn Glu Arg Gly Tyr Gly Ser Glu
945                 950                 955                 960
Ser Phe Glu Val Met Thr Thr Ser Lys Leu Leu Asn Val Ala Lys Ser
                965                 970                 975
Arg Glu Trp Tyr Arg Ala Asn Pro Asn Ile Asn Arg Glu Arg Arg Glu
                980                 985                 990
Leu Met Lys Trp Phe Leu Leu Lys Glu Asn Glu Tyr Leu Gly Gln Arg
            995                 1000                1005
Met Glu Lys Met Asp Ser Leu Glu Lys Ser
    1010                1015
```

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: protein ( i i i ) HYPOTHETICAL: YES ( i v ) ANTI-SENSE: NO ( v ) FRAGMENT TYPE: C-terminal ( v i ) ORIGINAL SOURCE:
        ( A ) ORGANISM: Plasmodium vivax ( v i i ) IMMEDIATE SOURCE:
        ( B ) CLONE: PvMB3.3.1

( i x ) FEATURE:
        ( B ) LOCATION: 2
        ( D ) OTHER INFORMATION: Leu or Met
        ( B ) LOCATION: 7
        ( D ) OTHER INFORMATION: Ala or Thr ( x i ) SEQUENCE DESCRIPTION: SEQ ID NO:3:

Asp    Xaa    Glu    Ala    Gly    Glu    Xaa    Glu
    1                                          5

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( i i i ) HYPOTHETICAL: YES ( i v ) ANTI-SENSE: NO ( v ) FRAGMENT TYPE: C-terminal ( v i ) ORIGINAL SOURCE:
        ( A ) ORGANISM: Plasmodium vivax ( v i i ) IMMEDIATE SOURCE:
        ( B ) CLONE: PvMB3.3.1

( x i ) SEQUENCE DESCRIPTION: SEQ ID NO:4:

Glu    Glu    Val    Glu    Glu    Val    Pro
    1                                        5

We claim:

1. An isolated purified peptide antigen comprising an amino acid sequence of PvESP-1, wherein said PvESP-1: (i) is a secreted blood-stage protein from *Plasmodium vivax*, (ii) is present in detectable amounts in biological samples of individuals infected with *Plasmodium vivax*, (iii) comprises an epitope not present in other Plasmodium species that cause malaria in humans, and (iv) binds monoclonal antibody 1D11G10;

said peptide antigen having the property of eliciting antibodies that recognize said PvESP-1.

2. An isolated purified peptide antigen comprising an amino acid sequence of PvESP-1 or a fragment thereof, wherein said PvESP-1: (i) is a secreted blood-stage protein from *Plasmodium vivax*, (ii) is present in detectable amounts in biological samples of individuals infected with *Plasmodium vivax* and (iii) binds monoclonal antibody 1D11G10;

said PvESP-1 or a fragment thereof comprising an epitope not present in other Plasmodium species that cause malaria in humans;

said peptide antigen having the property of eliciting antibodies that recognize said PvESP-1.

3. An isolated purified polypeptide comprising the amino acid sequence of SEQ ID NO: 2 or immunogenic *P. vivax* fragments thereof not present in other Plasmodium species that cause malaria in humans.

* * * * *